United States Patent [19]

Lubowitz et al.

[11] Patent Number: 5,082,905
[45] Date of Patent: Jan. 21, 1992

US005082905A

[54] BLENDED HETEROCYCLES

[75] Inventors: Hyman R. Lubowitz, Rolling Hills Estates, Calif.; Clyde H. Sheppard, Bellevue, Wash.

[73] Assignee: The Boeing Company, Seattle, Wash.

[21] Appl. No.: 696,492

[22] Filed: May 6, 1991

Related U.S. Application Data

[60] Division of Ser. No. 544,273, Jun. 26, 1990, which is a division of Ser. No. 116,592, Nov. 3, 1987, Pat. No. 4,965,336, which is a continuation-in-part of Ser. No. 816,490, Jan. 6, 1986, abandoned, which is a continuation-in-part of Ser. No. 651,826, Sep. 18, 1984, abandoned.

[51] Int. Cl.⁵ .................... C08F 283/00; C08G 69/48
[52] U.S. Cl. ..................... 525/420; 524/494; 524/495; 525/434; 525/435; 548/156; 548/220; 548/328; 548/431; 548/435; 548/476; 548/547; 528/170; 528/289; 528/298; 528/322; 528/329.1
[58] Field of Search ............. 525/420, 494, 495; 548/156, 220, 328, 435, 476, 547; 528/170, 289, 298, 322, 329.1

[56] References Cited

U.S. PATENT DOCUMENTS

| | | | |
|---|---|---|---|
| 3,267,081 | 8/1966 | Rudner et al. | 260/78.4 |
| 3,313,783 | 4/1967 | Iwakura et al. | 260/78 |
| 3,386,969 | 6/1968 | Levine | 260/78.4 |
| 3,689,464 | 9/1972 | Holub et al. | 260/78 |
| 3,729,446 | 4/1973 | Holub et al. | 260/47CZ |
| 3,748,311 | 7/1973 | Burns et al. | 260/78.4 R |
| 3,812,159 | 5/1974 | Lubowitz | 260/346.3 |
| 3,839,287 | 10/1974 | Kwiatkowski et al. | 260/49 |
| 4,107,174 | 8/1978 | Baumann et al. | 260/326 |
| 4,110,188 | 8/1978 | Darms et al. | 204/159 |
| 4,134,895 | 1/1979 | Roth et al. | 260/326 |
| 4,187,364 | 2/1980 | Darms et al. | 526/259 |
| 4,200,731 | 4/1980 | Massey et al. | 525/437 |
| 4,239,883 | 12/1980 | Stenzenberger | 528/322 |
| 4,250,096 | 2/1981 | Kvita et al. | 260/326 |
| 4,414,269 | 11/1983 | Lubowitz et al. | 428/290 |
| 4,423,202 | 12/1983 | Choe | 528/179 |
| 4,429,108 | 1/1984 | Stephens | 528/322 |
| 4,476,184 | 10/1984 | Lubowitz et al. | 428/288 |
| 4,476,295 | 10/1984 | Stephens | 528/322 |
| 4,533,692 | 8/1985 | Wolfe et al. | 524/417 |
| 4,533,693 | 8/1985 | Wolfe et al. | 524/417 |
| 4,533,724 | 8/1985 | Wolfe et al. | 528/313 |
| 4,536,559 | 8/1985 | Lubowitz et al. | 528/170 |
| 4,547,553 | 10/1985 | Lubowitz et al. | 525/384 |
| 4,578,470 | 3/1986 | Webb | 546/256 |
| 4,584,364 | 4/1986 | Lubowitz et al. | 528/128 |
| 4,604,437 | 8/1986 | Renner | 526/262 |
| 4,661,604 | 4/1987 | Lubowitz et al. | 548/435 |
| 4,684,714 | 8/1987 | Lubowitz et al. | 528/353 |
| 4,728,742 | 3/1988 | Renner | 548/435 |
| 4,739,030 | 4/1988 | Lubowitz et al. | 528/170 |
| 4,868,270 | 9/1989 | Lubowitz et al. | 528/170 |
| 4,965,336 | 10/1990 | Lubowitz et al. | 528/170 |

FOREIGN PATENT DOCUMENTS 2303818 1/1976 France .
53-40760 4/1978 Japan .

OTHER PUBLICATIONS

Sheppard et al., "Novel High Temperature Matrix Materials," Int. SAMPE Exhib. 1986, 31, Mater. Sci. Future 1426-1433, Eng.
EPO Search Report EP 88 10 0695, 8432.1

Primary Examiner—Morton Foelak
Attorney, Agent, or Firm—Senniger, Powers, Leavitt & Roedel

[57] ABSTRACT

Linear or multidimensional, crosslinking, solvent resistant oxazole, thiazole, or imidazole (i.e., heterocycle) oligomers and blends of the crosslinking oligomers and noncrosslinking comparable polymers are described. The oligomers are prepared by reacting tetraamines, diaminodiols, or diaminothiols (i.e. four-functional compounds) with poly-carboxylic acid halides, and crosslinking phenylimide end cap monomers in a suitable solvent under an inert atmosphere.

9 Claims, No Drawings

BLENDED HETEROCYCLES

REFERENCE TO RELATED APPLICATIONS

This application is a divisional of application Ser. No. 07/544,273, filed June 26, 1990 which is a division of application Ser. No. 07/116,592 filed Nov. 3, 1987, now U.S. Pat. No. 4,965,336 which is a continuation-in-part application based upon U.S. Ser. No. 816,490, filed Jan. 6, 1986, now abandoned, which was a continuation-in-part application based upon U.S. Ser. No. 651,826, filed Sept. 18, 1984, now abandoned.

TECHNICAL FIELD

The present invention relates to linear or multidimensional, solvent resistant, crosslinkable oligomers that include oxazole, thiazole, imidazole linkages along the oligomer backbone between mono- or difunctional crosslinking end-cap phenylimides of the general formula:

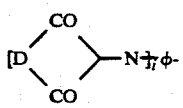

and to their method of manufacture.

BACKGROUND ART

Recently, chemists have sought to synthesize oligomers for high performance advanced composites suitable for aerospace applications. These composites should exhibit solvent resistance, be tough, impact resistant, and strong, be easy to process, and be thermoplastic. Oligomers and composites that have thermooxidative stability, and, accordingly can be used at elevated temperatures, are particularly desirable.

While epoxy-based composites are suitable for many applications, their brittle nature and susceptibility to degradation make them inadequate for many aerospace applications, especially those applications which require thermally stable, tough composites. Accordingly, research has recently focused upon polyimide composites to achieve an acceptable balance between thermal stability, solvent resistance, and toughness. The maximum use temperatures of conventional polyimide composites, such as PMR-15, are still only about 600° F.–625° F., since they have glass transition temperatures of about 690° F.

Linear polysulfone, polyether sulfone, polyester, and polyamide systems are also known, but each of these systems fails to provide as high thermal stability as is required in some aerospace applications.

There had been a progression of polyimide sulfone compounds synthesized to provide unique properties or combinations of properties. For example, Kwiatkowski and Brode synthesized maleic-capped, linear polyarylimides as disclosed in U.S. Pat. No. 3,839,287. Holub and Evans synthesized maleic- or nadic-capped, imido-substituted polyester compositions as disclosed in U.S. Pat. No. 3,729,446. We synthesized thermally stable polysulfone oligomers as disclosed in U.S. Pat. No. 4,476,184 or U.S. Pat. No. 4,536,559, and have continued to make advances with polyetherimidesulfones, polybenzoxazolesulfones (i.e., heterocycles), polybutadienesulfones, and "star" or "star-burst" multidimensional oligomers. We have shown surprisingly high glass transition temperatures and desirable physical properties in many of these oligomers and their composites, without losing ease of processing.

Multidimensional oligomers, such as disclosed in our copending applications U.S. Ser. No. 726,258; 810,817; and 000,605, are easier to process than many other advanced composite oligomers since they can be handled at lower temperatures. Upon curing, however, the unsaturated phenylimide end caps crosslink so that the thermal resistance of the resulting composite is markedly increased with only a minor loss of stiffness, matrix stress transfer (impact resistance), toughness, elasticity, and other mechanical properties. Glass transition temperatures above 950° F. are achieveable.

Commercial polyesters, when combined with well-known diluents, such as styrene, do not exhibit satisfactory thermal and oxidative resistance to be useful for aircraft or aerospace applications. Polyarylesters are unsatisfactory, also, since the resins often are semicrystalline which makes them insoluble in laminating solvents, intractable in fusion, and subject to shrinking or warping during composite fabrication. Those polyarylesters that are soluble in conventional laminating solvents remain so in composite form, thereby limiting their usefulness in structural composites. The high concentration of ester groups contributes to resin strength and tenacity, but also makes the resin susceptible to the damaging effects of water absorption. High moisture absorption by commercial polyesters can lead to distortion of the composite when it is loaded at elevated temperature.

High performance, aerospace, polyester advanced composites, however, can be prepared using crosslinkable, end-capped polyester imide ether sulfone oligomers that have an acceptable combination of solvent resistance, toughness, impact resistance, strength, ease of processing, formability, and thermal resistance. By including Schiff bas (—CH=N—), imidazole, thiazole, or oxazole linkages in the oligomer chain, the linear, advanced composites formed with polyester oligomers of our copending application U.S. Ser. No. 726,259 can have semiconductive or conductive properties when appropriately doped.

Conductive and semiconductive plastics have been extensively studied (see, e.g. U.S. Pat. Nos. 4,375,427; 4,338,222; 3,966,987; 4,344,869; and 4,344,870), but these polymers do not possess the blend of properties which are essential for aerospace applications. That is, the conductive polymers do not possess the blend of (1) toughness, (2) stiffness, (3) elasticity, (4) ease of processing, (5) impact resistance (and other matrix stress transfer capabilities), (6) retention of properties (over a broad range of temperatures), and (7) high temperature resistance that is desirable on aerospace advanced composites. These prior art composites are often too brittle.

Thermally stable multidimensional oligomers having semiconductive or conductive properties when doped with suitable dopants are also known and are described in our copending applications (including U.S. Ser. No. 773,381 to Lubowitz, Sheppard, and Torre). The linear arms of the oligomers contain conductive linkages, such as Schiff base (—N=CH—) linkages, between aromatic groups. Sulfone and ether linkages are interspersed in the arms. Each arm is terminated with a mono- or difunctional end cap (i.e., a radical having one or two crosslinking sites) to allow controlled crosslinking upon heat-induced or chemically-induced curing.

Polyamides of this same general type are described in U.S. Pat. No. 4,876,328; polyetherimides, in U.S. Pat. No. 4,851,495; and polyamideimides, in U.S. Ser. No. 092,740 which was abandoned in favor of U.S. Ser. No. 181,013.

SUMMARY OF THE INVENTION

The present invention relates to linear or multidimensional oxazole, thiazole, and imidazole (i.e., heterocycle) oligomers, particularly benzoxazole, benzothiazole, and benzimidazole oligomers, capped with mono- or difunctional end-cap monomers (i.e., monomers having one or two crosslinking sites) to achieve superior thermal stability while retaining desirable strength and physical properties.

The oligomers are usually prepared by the condensation of:

(a) 2 moles of a phenylimide carboxylic acid halide end-cap monomer of the general formula:

$$[D]_i\text{—}\phi\text{—}COX$$

wherein

D = is an unsaturated hydrocarbon radical as later defined herein.

i = 1 or 2; and $\phi$ = phenyl (b) n moles of a diacid halide particularly an aromatic dicarboxylic acid halide having a plurality of aryl groups intermediately linked by "sulfone" linkages and terminal carboxylic acid halide functionalities attached to the aryl groups; and (c) (n+1) moles of a four-functional compound of the formula:

$$\begin{array}{c} H_2N \quad NH_2 \\ \diagdown / \\ R \\ / \diagdown \\ Y \quad Y \end{array}$$

(such as a diaminodihydroxybenzene) wherein R is an hydrocarbon radical (preferably, an aromatic radical, if the highest thermal stability is sought); Y = —OH, —NH$_2$, or —SH; and the amine functionalities (—NH$_2$) are not substituted on the same carbon atom as the Y substituents.

The end-cap monomer preferably is selected from the group consisting of:

$$[D]_i\text{—}\phi\text{—}COX$$

wherein

D =

[chemical structures showing phenylimide and related imide end-cap radicals with (R$_1$)$_j$ substituents, G linkage, and carbonyl groups]

-continued

[additional chemical structures showing various imide end-cap radicals with (R$_1$)$_j$, Me, O, and T substituents]

R$_1$ = lower alkyl, aryl, substituted aryl (including hydroxyl or halo-substituents), lower alkoxy, aryloxy, halogen, or mixtures thereof (preferably lower alkyl);

X = halogen, preferably Cl;

G = —SO$_2$—, —S—, —O—, or —CH$_2$—;

i = 1 or 2;

j = 0, 1, or 2;

$\phi$ = phenyl;

T = methallyl or allyl; and

Me = methyl.

Preferred end-cap monomers are the phenylimide acid halides where D includes a radical selected from:

[chemical structures showing HC≡C-phenyl and bicyclic R″-substituted radicals]

wherein R″ is hydrogen or lower alkyl.

Blended oligomers are prepared to include the crosslinking oligomers and at least one comparable, non-crosslinking polymer. The polymer generally has a substantially identical backbone to the oligomer, but is terminated (or quenched) with a monomer that is unable to crosslink. Accordingly, the comparable copolymer is generally prepared by condensing:

(a) 2 moles of an acid halide end-cap quenching monomer;

(b) n moles of the diacid halide of the crosslinking oligomer;

(c) (n+1) moles of the four-functional compound of the crosslinking oligomer.

A suitable monomer for quenching the polymerization reaction for the comparable oligomer is benzoic acid halide

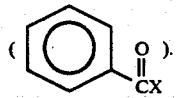

Of course, the crosslinking oligomers can also be prepared by the condensation of:

(a) 2 moles of a phenylimide amine, phenol, or sulfhydryl (i.e., thio) monomer;

(b) n moles of a four-functional compound; and (c) (n+1) moles of a suitable diacid halide.

The comparable polymer could also include the analogous backbone and could be quenched with a phenol or suitable thio- or amino-monomer (such as aniline).

Generally, the four-functional compound is selected from the group consisting of:

dihydroxybenzidine;
dimercaptobenzidine;
2,6-diamino-3,5-dihydroxybenzene;
2,6-diamino-3,5-dimercaptobenzene; or
diaminobenzidine.

Heterocycle oligomers of this general type are easily processed into prepregs and composites. The composites (or laminates) are chemically, thermally, and dimensionally stable at relatively high temperatures and exhibit solvent-resistance.

Multidimensional oligomers can be prepared by reacting the four-functional compounds and phenylimide acid halide end-cap monomers with an aromatic hub having 3 or more reactive acid halide functionalities, such as a compound of the formula:

wherein
Ar=an aromatic moiety of valance w, and
w=an integer greater than or equal to 3, and generally 3 or 4.

The hub (Ar) may be a residue of cyuranic acid or an imide/acid compound formed by reacting, for example, triaminobenzene with phthalic acid anhydride or a corresponding acid anhydride. The arms of the multidimensional oligomers can be extended by adding diacid halides to the reaction mixture, as will be understood. Corresponding ether/acid hubs can be prepared by condensing a phenolic hub, like phloroglucinol with nitrobenzoic acid or with nitrophthalic acid. Blends of multidimensional oligomers and corresponding polymers can also be prepared.

BEST MODE CONTEMPLATED FOR CARRYING OUT THE INVENTION

The crosslinking oligomers of the present invention are oxazoles, thiazoles, or imidazoles (i.e. heterocycles) generally prepared by the condensation of:

(a) 2 moles of a phenylimide carboxylic acid halide end-cap monomer;

(b) n moles of a diacid halide, particularly an aromatic dicarboxylic acid halide having a plurality of aryl groups intermediately linked by "sulfone" (i.e., electronegative) linkages and terminal acid halide functionalities attached to aryl groups; and (c) (n+1) moles of a four-functional compound of the formula:

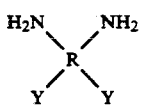

wherein R is a hydrocarbon radical (preferably an aromatic radical), Y=—OH, —SH, or —NH₂, and the Y and —NH₂ are on separate carbon atoms. Generally, the amine and Y are on adjacent carbon atoms of an aromatic ring. The four-functional compound, accordingly, is generally selected from the group consisting of:

dihydroxybenzidine;
dimercaptobenzidine;
2,6-diamino-3,5-dihydroxybenzene;
2,6-diamino-3,5-dimercaptobenzene; or
diaminobenzidine.

The end-cap monomer generally is selected from the group consisting of:

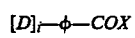

wherein
D=

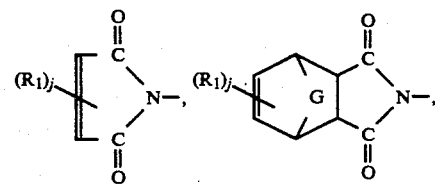

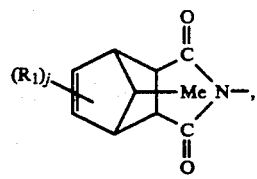

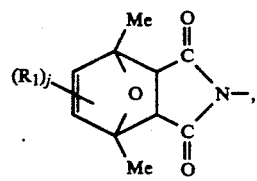

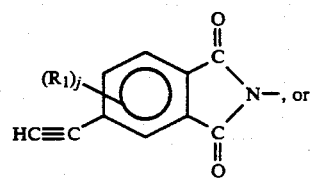

-continued

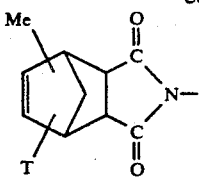

$R_1$ = lower alkyl, aryl, substituted aryl (including hydroxyl or halo-substituents), lower alkoxy, aryloxy, halogen, or mixtures thereof (preferably lower alkyl);
X = halogen;
φ = phenyl;
G = —O—, —S—, —SO$_2$—, or —CH$_2$—;
i = 1 or 2;
j = 0, 1, or 2;
T = methallyl or allyl; and
Me = methyl.

(c) biphenyl;
(d) a polyaryl "sulfone" divalent radical of the general formula:

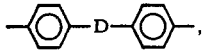

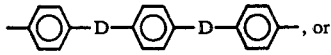

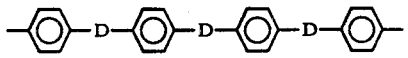

wherein D = —S—, —O—, —CO—, —SO$_2$—, —(CH$_3$)$_2$C—, —(CF$_3$)$_2$C—, or mixtures thereof throughout the chain; or
(e) a divalent radical having conductive linkages, illustrated by Schiff base compounds selected from the group consisting of:

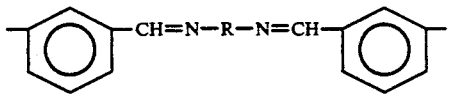

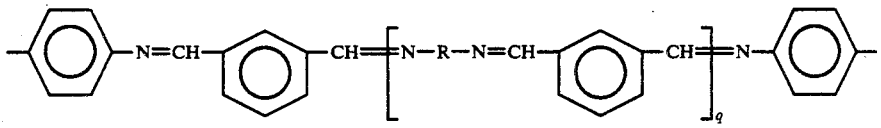

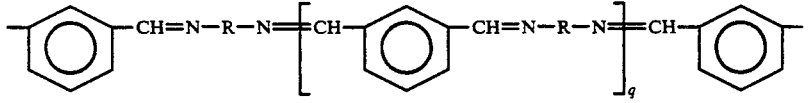

These end-cap monomers have hydrocarbon unsaturation to provide one or two crosslinking sites. For the highest thermal stability, D includes a radical selected from:

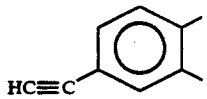

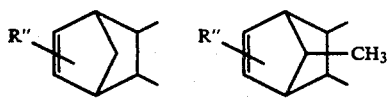

wherein R" is hydrogen or lower alkyl.

The reaction is generally carried out at an elevated temperature under an inert atmosphere (dry N$_2$ purge) in a suitable solvent including an excess of base (KOH or NaOH) to reduce the possibility of undesirable side reactions that might otherwise occur in an acidic solution. Usually about 10% excess base is added, based upon the molar quantities of the reactants.

The dicarboxylic acid halide (or dicarboxylic acid) may include an aromatic chain segment selected from the group consisting of:
(a) phenyl;
(b) naphthyl;

wherein R is selected from the group consisting of: phenyl; biphenyl; naphthyl; or a divalent radical of the general formula:

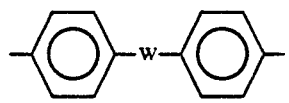

wherein W = —SO$_2$— or —CH$_2$—; and q = 0–4; or
(f) a divalent radical of the general formula:

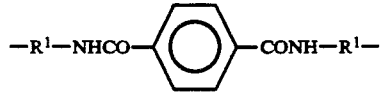

wherein $R^1$ = a $C_2$ to $C_{12}$ divalent aliphatic, alicyclic, or aromatic radical, and, preferably, phenyl (as described in U.S. Pat. No. 4,556,697).

Thiazole, oxazole, or imidazole linkages, especially between aryl groups, may also be used in the conductive or semiconductive oligomers, instead of the Schiff base linkages. The oligomers being heterocycles, may be semiconductive upon doping even without incorporating additional conductive linkages.

The diacid halide preferably is an aromatic dicarboxylic acid selected from the group consisting of:

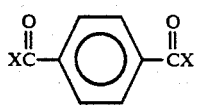
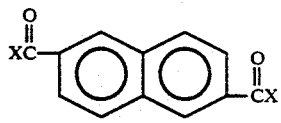
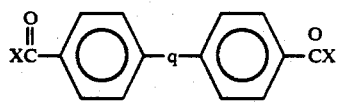
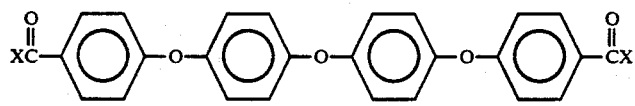
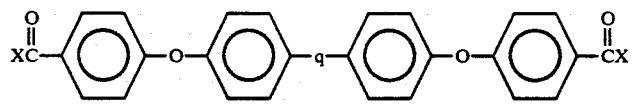
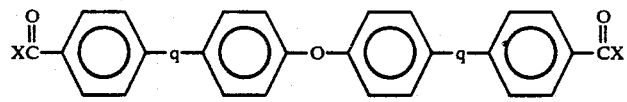
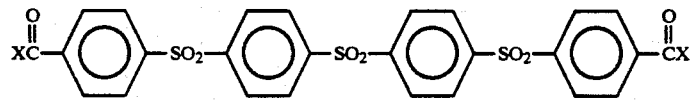
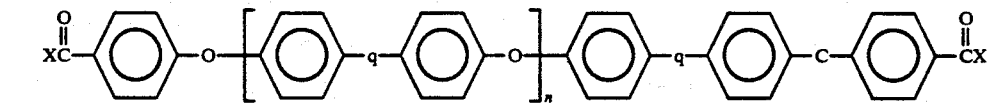
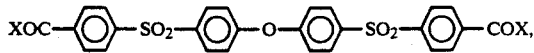
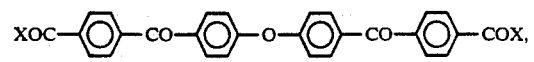
wherein q is an electronegative ("sulfone") group, preferably —CO—, —S—, —(CF$_3$)$_2$C—, or —SO$_2$, and, generally, —CO—, —SO$_2$—; and m equals a small integer generally from 1–5.
Preferred diacid halides include:

-continued

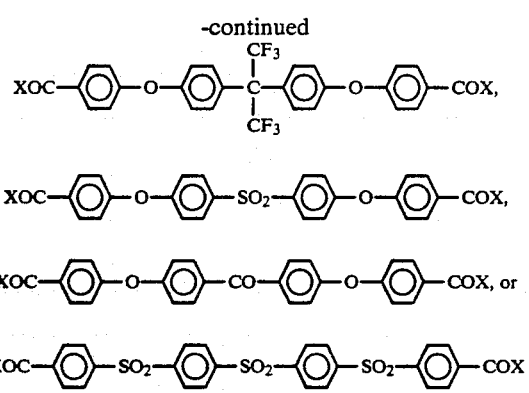

Schiff base dicarboxylic acids and diacid halides can be prepared by the condensation of aldehydes and aminobenzoic acid (or other amine acids) in the general reaction scheme:

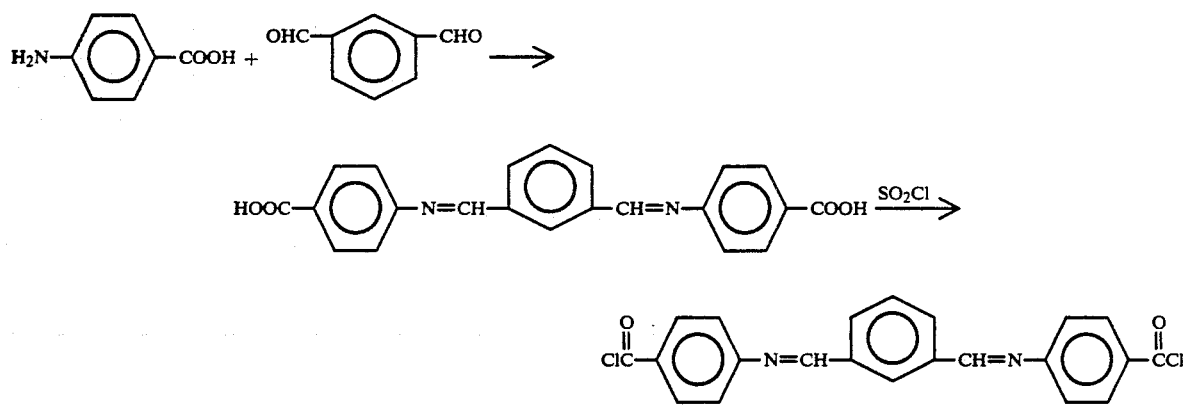

or similar syntheses.

Other diacid halides that can be used, but that are not preferred, are disclosed in U.S. Pat. No. 4,504,632, and include:

adipylchloride,
malonyl chloride,
succinyl chloride,
glutaryl chloride,
pimelic acid dichloride,
suberic acid dichloride,
azelaic acid dichloride,
sebacic acid dichloride,
dodecandioic acid dichloride,
phthaloyl chloride,
isophthaloyl chloride,
terephthaloyl chloride,
1,4-naphthalene dicarboxylic acid dichloride, and
4,4′-diphenylether dicarboxylic acid dichloride.

Polyaryl or aryl diacid halides are preferred to achieve the highest thermal stabilities in the resulting oligomers and composites because aliphatic bonds are not as thermally stable as aromatic bonds. Particularly preferred compounds include intermediate "sulfone" (i.e. electronegative) linkages to improve the toughness of the resulting oligomers. For purposes of this description, "sulfone" linkage should be understood to include —SO$_2$—, —S—, —CO—, and —(CF$_3$)$_2$C—, unless clearly limited to only —SO$_2$—.

Suitable diacid halides include compounds made by reacting nitrobenzoic acid with a bisphenol (i.e., dihydric phenol, dialcohol, or diol). The bisphenol is preferably selected from the group consisting of:

2,2-bis-(4-hydroxyphenyl)-propane (i.e., bisphenol-A);
-bis-(2-hydroxyphenyl)-methane;
bis-(4-hydroxyphenyl)-methane;
1,1-bis-(4-hydroxyphenyl)-ethane;
1,2-bis-(2-hydroxyphenyl)-ethane;
1,1-bis-(3-chloro-4hydroxyphenyl)-ethane;
1,1-bis-(3,5-dimethyl-4-hydroxyphenyl)-ethane;
2,2-bis-(3-phenyl-4-hydroxyphenyl)-propane;
2,2-bis-(4-hydroxynaphthyl)-propane;
2,2-bis-(4-hydroxyphenyl)-pentane;
2,2-bis-(4-hydroxyphenyl)-hexane;
bis-(4-hydroxyphenyl)-phenylmethane;
bis-(4-hydroxyphenyl)-cyclohexylmethane;
1,2-bis-(4-hydroxyphenyl)-1,2-bis-(phenyl)-ethane;
2,2-bis-(4-hydroxyphenyl)-1-phenylpropane;
bis-(3-4-hydroyphenyl)-methane;
bis-(4hydroxy-2,6-dimethyl-3-methoxyphenyl)-methane;
2,2-bis-(3,5-dichloro-4-hydroxyphenyl)-propane;
2,2-bis-(3-bromo-4-hydroxyphenyl)-propane;

or mixtures thereof, as disclosed in U.S. Pat. No. 3,262,914. Bisphenols having aromatic character (i.e., absence of aliphatic segments), such as bisphenol-A, are preferred.

The bisphenol may be in phenate form, or a corresponding sulfyhydryl can be used. Of course, mixtures of bisphenols and disulfhydryls can be used.

Other suitable bisphenols are described in our copending application Ser. Nos. 016,703 and 726,258; or in U.S. Pat. Nos. 4,584,364; 4,661,604; 3,262,914, or 4,611,048.

While bisphenol-A is preferred (because of coast and availability), the other bisphenols can be used to add rigidity to the oligomer without significantly increasing the average formula weight, and therefore, can increase the solvent resistance. Random or block copolymers are possible.

Bisphenols of the type described are commercially available. Some may be easily synthesized by reacting dihalogen intermediate with bis-phenates, such as the reaction of 4,4′-dichlorophenyl-sulfone with bis(-disodium biphenolate). Preferred dihalogens in this circumstance are selected from the group consisting of:

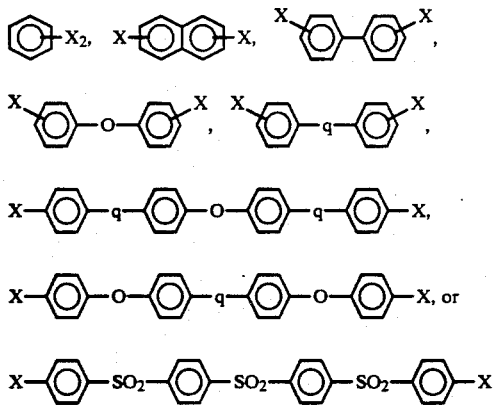

wherein X=halogen, preferably chlorine; and q=—S—, —SO$_2$—, —CO—, —(CH$_3$)$_2$—, and —(CF$_3$)$_2$C—, and preferably either —SO$_2$— or —CO—.

the heterocycle oligomers of the present invention can also be prepared by the condensation of:

(a) 2 moles of a crosslinking phenylimide amine, phenol, or sulfhydryl end-cap monomer;
(b) n moles of the four functional compound; and
(c) (n+1) moles of a suitable diacid halide.

In this case, the end-cap monomer generally has the formula:

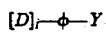

wherein D, i, and $\phi$ are previously defined and Y=—OH, —SH, or —NH$_2$.

Blends can improve impact resistance of composites without causing a significant loss of solvent resistance. The blends comprise mixtures of one or more crosslinkable oligomer and one or more polymer that is incapable of crosslinking. Generally, the blends comprise substantially equimolar amounts of one polymer and one oligomer having substantially identical backbones. The crosslinkable oligomer and comparable polymer can be blended together by mixing mutually soluble solutions of each. While the blend is preferably equimolar in the oligomer and polymer, the ratio of the oligomer and polymer can be adjusted to achieve the desired physical properties.

Although the polymer in such a blend usually has the same length backbone as the oligomer, the properties of the composite formed from the blend can be adjusted by altering the ratio of formula weights for the polymer and oligomer. The oligomer and polymer generally have substantially identical repeating units, but the oligomer and polymer merely need be compatible in the solution prior to sweeping out as a prepreg. Of course, if the polymer and oligomer have identical backbones, compatibility in the blend is likely to occur. Blends that comprise relatively long polymers and relatively short oligomers (i.e., polymers having higher average formula weights than the oligomers) prior to curing are preferred, since, upon curing, the oligomers will effectively increase in MW by crosslinking.

In synthesizing the comparable polymers, quenching end caps can be employed, if desired, to regulate the polymerization of the comparable polymer, so that it has an average formula weight substantially identical with the crosslinkable oligomer. For thermal stability, an aromatic compound, such as aniline or benzoic acid chloride, is preferred to quench the synthesis.

Solvent resistance may decrease markedly if the comparable polymer is provided in large excess to the crosslinkable oligomer in the blend.

The blends will generally comprise a mixture of a heterocycle oligomer and the same heterocycle polymer (i.e., oxazole oligomer and oxazole polymer). The polymer may, however, be a different heterocycle, such as an imide, imidazole, or thiazole. The mixture may include several types of oligomers or several types of polymers, such as a three component mixture of an oxazole oligomer, a thiazole oligomer, and an imidazole polymer.

The blends may be semi-interpenetrating networks of the general type described by Egli et al, "Semi-Interpenetrating Networks of LARC-TPI" available from NASA-Langley Research Center.

Because the oligomers synthesized in accordance with this invention generally have appreciable molecular weight between the reactive (crosslinking) groups, the oligomers will retain sufficient plasticity to be processible during fabrication prior to crosslinking of the end caps to thermoset composites. If possible, thermoplastic formulations with high molecular weights should be synthesized so long as the oligomers retain the necessary solubility. The oligomers preferably have MWs (i.e., average formula weights) between about 5000–40,000, and, more preferably, between about 15,000–25,000. Thermosetting heterocycle oligomers of the present invention generally will have average formula weights of between about 500–5000. Mixtures of oligomers having molecular weights within these ranges may also be used, for example, a mixture of an oligomer having a molecular weight of about 1,000 with an oligomer having a molecular weight of about 20,000, or a mixture of an oligomer with a molecular weight of about 5,000 with an oligomer having a molecular weight of about 10,000 or about 20,000. Within the described ranges, the oligomers can be crosslinked to form solvent resistant composites of high thermal stability suitable for many aerospace applications. The oligomers, however, are relatively soluble, and, therefore, may be easily processed, into prepregs by conventional steps.

Solubility of the oligomers becomes an increasing problem as chain length increases. Therefore, shorter chains are preferred, if the resulting oligomers remain processible. That is, the chains should be long enough to yield thermoplastic characteristics to the oligomers but short enough to keep the oligomers soluble during the reaction sequence.

Linear heterocycle oligomers preferably are synthesized using a diacid halide selected from the group consisting of:

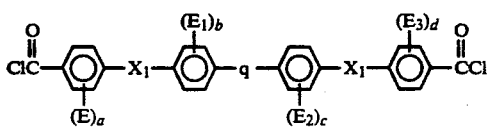

wherein q is selected from the group consisting of —(CF$_3$)$_2$C—, —SO$_2$—, —S—, or —CO—; X$_1$ is selected from the group consisting of —O— or —SO$_2$—; E, E$_1$, E$_2$ and E$_3$ each represent substituent groups selected from the group consisting of halogen, alkyl groups having 1 to 4 carbon atoms, and alkoxy groups having 1 to 4 carbon atoms, and "a", "b", "c", and "d" are all integers having values from 0 to 4.

The compound:

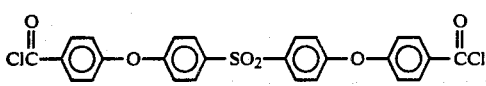

is particularly preferred, especially if the end-cap monomer is either:

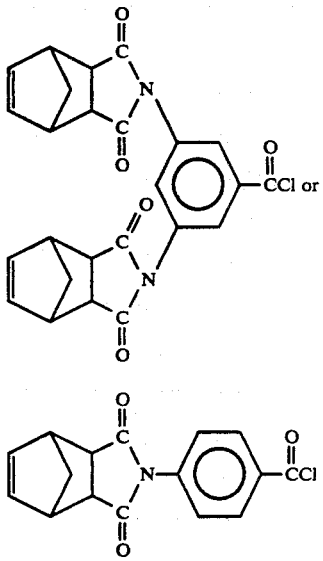

Multidimensional oligomers may be synthesized using an aromatic hub, such as cyuranic acid (or its acid halide), the four functional compounds, and the acid halide end-cap monomers. The oligomers have the general formula:

wherein
Ar = the aromatic hub residue;
M = a monovalent radical having at least one heterocycle (oxazole, thiazole, or imidazole) linkage and at least one, terminal, crosslinking functionality; and
w = an integer greater than or equal to 3, and preferably 3 or 4.

The chains within each arm (M) can be extended by including diacid halides in the reaction mixture.

In multidimensional oligomers, an aromatic hub includes a plurality of rays or spokes radiating from the hub in the nature of a star to provide multidimensional crosslinking through suitable terminal groups with a greater number (i.e. higher density) of crosslinking bonds than linear arrays provide. Usually the hub will have three radiating chains to form a "Y" pattern. In some cases, four chains may be used. Including more chains leads to steric hindrance as the hub is too small to accommodate the radiating chains. A trisubstituted phenyl hub is highly preferred with the chains being symmetrically placed about the hub. Biphenyl, naphthyl, or azaline (e.g., melamine) may also be used as the hub radical along with other aromatic moieties, if desired.

Triazine derivatives can be used as the hub. These derivatives are described in U.S. Pat. No. 4,574,154 and have the general formula:

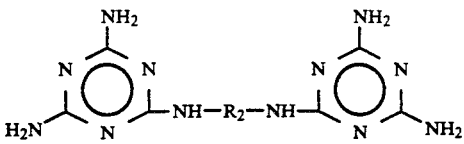

wherein $R_2$ is a divalent hydrocarbon residue containing 1-12 carbon atoms (and, preferably, ethylene) by reacting the amine functionalities with phthalic acid anhydride to form arms that include imide linkages and terminal acid functionalities (that can be converted to acid halides, if described). The triazine derivatives of U.S. Pat. No. 4,617,390 (or the acid halides) can also be used as the hub.

Hubs suitable for making multidimensional, heterocycle oligomers of the present invention can be made by reacting polyol aromatic hubs, such as phloroglucinol, with nitrobenzoic acid or nitrophthalic acid to form either linkages and active, terminal carboxylic acid functionalities. The nitrobenzoic acid products would have three active sites while the nitrophthalic acid products would have six; each having the respective formula:

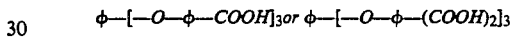

wherein $\phi$ = phenyl. Of course other nitro-acids can be used.

Hubs can also be formed by reacting the corresponding halo-hub (such a tribromobenzene) with aminophenol to form triamine compounds represented by the formula:

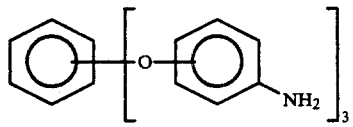

which can then be reacted with an acid anhydride to form a polycarboxylic acid of the formula:

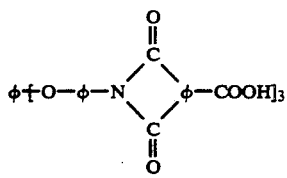

wherein $\phi$ = phenyl; the hub being characterized by an intermediate ether and imide linkage connecting aromatic groups. Thio-analogs are also contemplated, in accordance with U.S. Pat. No. 3,933,862.

Phenoxyphenyl sulfone arms radiating from a hub with either an amine or carboxylic acid are also precursors for making multidimensional heterocycle oligomers of the present invention.

The best results are likely to occur when the hub is cyuranic acid, and when a four-functional compound and end-cap monomer are reacted with the hub to form a short armed oligomer having three or six crosslinking sites. These compounds are the simplest multidimensional oligomers and are relatively inexpensive to synthesize.

Blends of the multidimensional oligomers, comparable to the blends of linear oligomers, can also be prepared, as will be understood.

The oligomers can be synthesized in a homogeneous reaction scheme wherein all the reactants are mixed are one time, or in a stepwise reaction scheme wherein the radiating chains are affixed to the hub and the product of the first reaction is subsequently reacted with the end cap groups. Of course, the hub may be reacted with end-capped arms that include one reactive, terminal functionality for linking the arm to the hub. Homogeneous reaction is preferred, resulting undoubtedly in a mixture of oligomers because of the complexity of the reactions. The products of the processes (even without distillation or isolation of individual species) are preferred oligomer mixtures which can be used without further separation to form the desired advanced composites.

If the linear or multidimensional oligomers include Schiff base or other conductive linkages, the composites may be conductive or semiconductive when suitably doped. The dopants are preferably selected from compounds commonly used to dope other polymers, namely, (1) dispersions of alkali metals (for high activity) or (2) strong chemical oxidizers, particularly alkali perchlorates (for lower activity). Arsenic compounds and elemental halogens, while active dopants, are too dangerous for general usage, and are not recommended.

The dopants apparently react with the oligomers or polymers to form charge transfer complexes. N-type semiconductors result from doping with alkali metal dispersions. P-type semiconductors result from doping with elemental iodine or perchlorates. Dopant should be added to the oligomer or blend prior to forming the prepreg.

While research into conductive or semiconductive polymers has been active, the resulting compounds (mainly polyacetylenes, polyphenylenes, and polyvinylacetylenes) are unsatisfactory for aerospace applications because the polymers are:
 (a) unstable in air;
 (b) unstable at high temperatures;
 (c) brittle after doping;
 (d) toxic because of the dopants; or
 (e) intractable.
These problems are overcome or significantly reduced with the conductive oligomers of the present invention.

While conventional theory holds that semiconductive polymers should have (1) low ionization potentials, (2) long conjugation lengths, and (3) planar backbones, there is an inherent trade-off between conductivity and toughness or processibility, if these constraints are followed. To overcome the processing and toughness shortcomings common with Schiff base, oxazole, imidazole, or thiazole polymers, the oligomers of the present invention generally include "sulfone" linkages interspersed along the backbone providing a mechanical swivel for the rigid, conductive segments of the arms.

Because the heterocycle (oxazole, thiazole, or imidazole) linkages are themselves within the family of conductive or semiconductive linkages, it may be unnecessary to include Schiff base linkages to achieve conductive or semiconductive properties upon doping. That is, conductive or semiconductive properties might be achieved simply be doping the oxazole, thiazole, or imidazole oligomers.

Linear or multidimensional oligomers can be synthesized from a mixture of four or more reactants so that extended chains may be formed. Adding components to the reaction mixture, however, adds to the complexity of the reaction and of its control. Undesirable competitive reactions may result or complex mixtures of macromolecules having widely different properties may be formed, because the chain extenders and chain terminators are mixed, and compete with one another.

All reactions should be conducted under an inert atmosphere and at elevated temperatures, if the reaction rate needs to be increased. The reaction mixture should be well stirred throughout the synthesis. Chilling the reaction mixture can slow the reaction rate and can assist in controlling the oligomeric product.

While para isomerization is shown for all of the reactants, other isomers are possible. Furthermore, the aryl groups can have substituents, if desired, such as halogen, lower alkyl up to about 4 carbon atoms, lower alkoxy up to about 4 carbon atoms, or aryl. Substituents may create steric hindrance problems in synthesizing the oligomers or in crosslinking the oligomers into the final composites.

The following examples are presented to illustrate various features of the invention.

EXAMPLE I

Synthesis of bis(3-methylphenoxyphenyl) sulfone

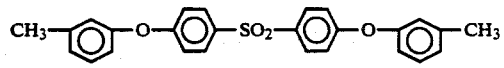

A one liter bottle fitted with a stirrer, thermometer, Barrett trap, condenser, and nitrogen inlet tube was charged with 88.3 grams (0.82 moles) of m-cresol, 286.6 grams of dimethyl sulfoxide (DMSO), 134.8 grams of toluene, and 65.3 grams of a 50% NaOH solution. The mixture was heated to 127° C. and the water was removed. The mixture was then heated to 165° C. to remove the toluene, and was cooled to 110° C. before adding 111.7 grams (0.39 moles) of dichlorodiphenylsulfone. The mixture was heated for 4 hours at 141° C., before the mixture was poured into 3 liters of water to crystallize an intermediate. The water was decanted, and 1 liter of 2-propanol was added. This mixture was heated until the majority of the product dissolved. The product was recrystallized, recovered by filtration, washed with 3 liters of water followed by 500 ml of 2-propanol, and dried. 167.4 grams of a bis(2-methylphenoxyphenyl) sulfone product resulted. The melting point ranged from 83° C.–85° C.

EXAMPLE II

Synthesis of bis(3-carboxyphenoxyphenyl) sulfone

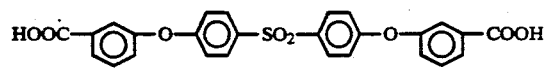

A reaction flask fitted with a stirrer, condenser, thermometer, and N$_2$ purge was charged with 100 grams of the product of Example I, 775 grams of pyridine, and 155 grams of water. The mixture was refluxed and oxidized with 49 grams of KMnO$_4$, filtered to recover the intermediate to which 775 grams of 1.8 N NaOH solution was added. The mixture was refluxed, oxidized, and filtered again. The oxidation steps were repeated 5 times. The resulting final product had a melting point ranging from about 213.5° C. to 219° C.

EXAMPLE III

Synthesis of the acid chloride of the product obtained in Example II $CH_2Cl_2$ using petroleum ether, was washed with petroleum ether, and washed again with methanol. The product yield was 82%, and the product had a a melting range of 220° C.-245° C.

EXAMPLE V

Synthesis of nadic dicapped polybenzoxazole. Formula weight approximately 2,410

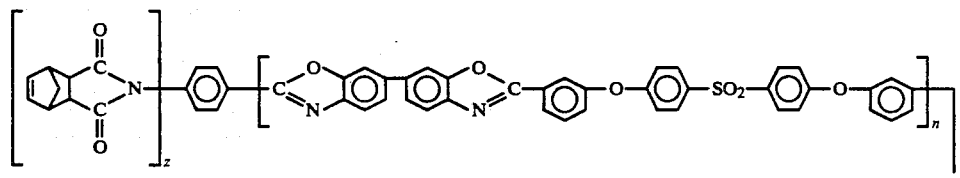

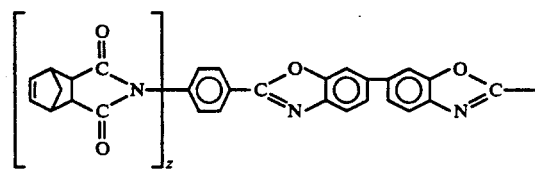

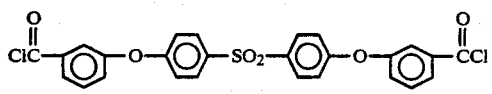

Twenty grams of the product of Example II was mixed with 61.2 grams of $SO_2Cl$ in a reaction flask, fitted with a stirrer, condenser, thermometer, and dry $N_2$ purge. The mixture was refluxed for 2 hours and the $SO_2Cl$ was distilled off. Two hundred ml of benzene was added and the mixture was refluxed, cooled, and filtered to recover the raw product which was recrystallized to a powder. The powder was mixed with 200 ml of benzene, refluxed, and cooled to form a precipitate that had a melting range of about 115° C. 118° C.

EXAMPLE IV

Synthesis of nadic dicapped polybenzoxazole. Formula weight approximately 4,000

12.53 grams (23.76 m-moles) of the acid chloride terminated sulfone in Example III was combined with 7.71 grams (35.65 m-moles) of 3,3'-dihydroxybenzidine in pyridine. The mixture was stirred under nitrogen in an ice water bath. 11.00 grams (23.76 m-moles) of nadic dicapped acid chloride in $CH_2Cl_2$ was added over a 30-minute period, and the mixture was stirred 3 hours at room temperature.

The product was precipitated in a blender with water, recovered with filtration, washed with water, and then washed again with methanol. The product was dried under nitrogen, and had a melting point of about 245° C.

EXAMPLE VI

General method of preparation of composites for oligomer of Example IV

The resulting oligomers were impregnated on epoxy-

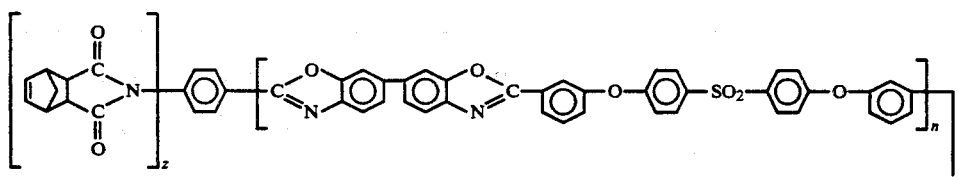

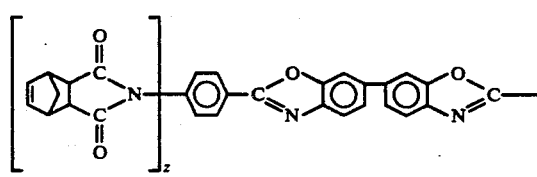

5.62 grams (10.66 mmoles) of the acid chloride terminated sulfone of Example III was combined with 2.47 grams (5.3 mmoles) of nadic dicapped acid chloride in $CH_2Cl_2$. The mixture of acid chlorides was added using an addition funnel to a stirred slurry of 2.88 grams (13.3 mmoles) of 3,3'-dihydroxybenzidine in dimethylacidamide (DMAC). The mixture was stirred for 3 hours at room temperature, and then sat under $N_2$ for 48 hours in the atmosphere. The product was recrystallized from sized T300/graphite fabric style (Union Carbide 35 million modulus fiber 24×24 weave). The solution obtained in each Example was coated onto the dry graphite fabric so that 38% by weight of the resulting prepreg would be the oligomer. The prepreg was allowed to dry under ambient conditions to less than 1% volatile content. The prepreg was then cut into 6×6-inch pieces and stacked to obtain a consolidated composite of approximately 0.062-inch. The stack of prepreg was then vacuum bagged and consolidated under a bag pressure of 200 psi for 3 hours at 650° F. and for two hours thereafter in an autoclave.

EXAMPLE VII

A polybenzoxazole oligomer was made using the procedure described in Examples IV and V. Composite panels were fabricated as described in Example VI, and the mechanical properties of each panel were determined. Table I illustrates the mechanical properties.

TABLE I

Summary Mechanical Properties of Polybenzoxazole Oligomers

| Panel Resin Example No. | FMW | Cure T °F. | Shear Strength psi (1) at: | | |
|---|---|---|---|---|---|
| | | | RT | 450° F. | 650° F. |
| Example IV | 4000 | 650 | 3460 | — | — |
| Exmaple V | 2500 | 650 | 4720 | 4090 | 2680 |

(1) Short beam shear test method.

While preferred embodiments have been described, those skilled in the art will recognize alternations, variations, or modifications that might be made to the embodiments without departing from the inventive concept. The description and examples, accordingly, are meant to illustrate the invention. The claims should be interpreted liberally in view of the description, and should be limited only as is necessary in view of the pertinent prior art.

We claim:

1. A blend comprising a crosslinking oligomer and a comparable noncrosslinking polymer, the crosslinking oligomer formed by reacting:

(a) 2 moles of a crosslinking phenylimide acid halide of the general formula:

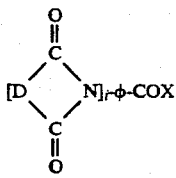

wherein
   D=is an unsaturated hydrocarbon radical;
   i=1 or 2; and
   $\phi$=phenyl (b) n moles of a diacid halide; and
   (c) (n+1) moles of at least one four-functional compound of the general formula:

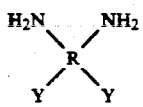

wherein R is a hydrocarbon radical, Y is selected from the group consisting of —OH, —SH and —NH$_2$, each Y group is attached to a carbon atom adjacent to a carbon atom to which the —NH$_2$ group is attached, and n is selected so that the oligomer has an average formula weight of between about 500 to about 40,000.

2. The blend of claim 1 wherein:

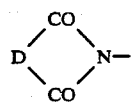

is a radical selected from the group consisting of:

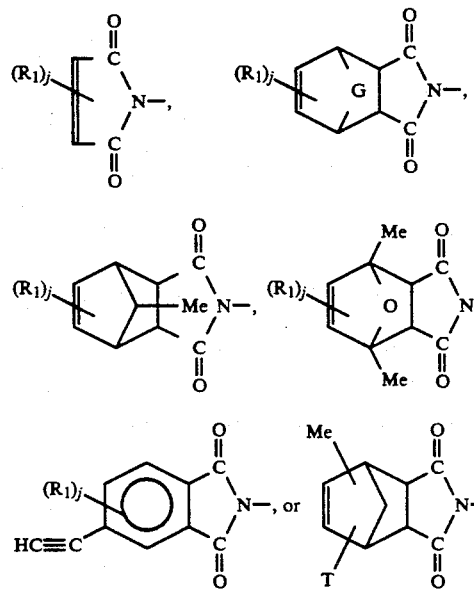

wherein
R$_1$=lower alkyl, lower alkoxy, aryl, aryloxy, substituted alkyl, substituted aryl, halogen, or mixtures thereof;
j=0,1, or 2;
G=—CH$_2$—, —O—, —S—, or —SO$_2$—;
T=methallyl or allyl; and
Me=methyl.

3. The blend of claim 1 wherein the backbones of both the oligomer and the polymer include benzoxazole linkages.

4. The blend of claim 1 wherein the backbones of both the oligomer and the polymer include benzimidazole linkages.

5. The blend of claim 1 wherein the backbones of both the oligomer and the polymer include benzothiazole linkages.

6. The blend of claim 1 comprising substantially equimolar amounts of the oligomer and polymer.

7. The blend of claim 1 wherein the oligomer and polymer have substantially identical backbones.

8. A prepreg comprising the blend of claim 1 and a reinforcing additive in fiber or particulate form.

9. A composite comprising the cured prepreg of claim 8.

* * * * *